United States Patent [19]

Weber et al.

[11] Patent Number: 5,064,508

[45] Date of Patent: Nov. 12, 1991

[54] PROCESS FOR THE SEPARATION OF 2-METHYLALKANALS FROM ISOMERS THEREOF

[75] Inventors: Jurgen Weber, Oberhausen; Peter Lappe, Dinslaken; Helmut Springer, Oberhausen, all of Fed. Rep. of Germany

[73] Assignee: Hoechst Aktiengesellschaft, Oberhausen, Fed. Rep. of Germany

[21] Appl. No.: 574,609

[22] Filed: Aug. 28, 1990

Related U.S. Application Data

[63] Continuation of Ser. No. 325,660, Mar. 20, 1989, abandoned.

[30] Foreign Application Priority Data

Mar. 31, 1988 [DE] Fed. Rep. of Germany ....... 3811039

[51] Int. Cl.$^5$ .............................................. B01D 3/34
[52] U.S. Cl. .............................. 203/38; 203/DIG. 6; 568/492
[58] Field of Search ....................... 203/38, 34, 61, 59, 203/62, DIG. 6, 91; 568/492

[56] References Cited

U.S. PATENT DOCUMENTS

| | | | |
|---|---|---|---|
| 4,054,555 | 10/1977 | Ackermann et al. | 568/492 |
| 4,408,079 | 10/1983 | Merger et al. | 568/463 |
| 4,496,770 | 1/1985 | Duembgen et al. | 568/463 |
| 4,677,230 | 6/1987 | Hupfer et al. | 568/450 |
| 4,678,857 | 7/1987 | Dureanleau et al. | 568/492 |
| 4,922,028 | 5/1990 | Oswald et al. | 568/448 |

FOREIGN PATENT DOCUMENTS

| | | |
|---|---|---|
| 960187 | 9/1956 | Fed. Rep. of Germany . |
| 2218305 | 10/1973 | Fed. Rep. of Germany . |
| 2459152 | 1/1977 | Fed. Rep. of Germany . |
| 2833538 | 9/1984 | Fed. Rep. of Germany . |
| 2078748 | 1/1982 | United Kingdom . |

OTHER PUBLICATIONS

New Syntheses With Carbon Monoxide: Edited by J. Falbe, 1980 pp. 3–59.

*Primary Examiner*—Virginia Manoharan
*Attorney, Agent, or Firm*—Charles A. Muserlian

[57] ABSTRACT

A process for the separation of 2-methylalkanals from a mixture thereof with at least one alpha unbranched aldehyde thereof comprising distillation of said mixture in the presence of formaldehyde and an aldolization catalyst whereby the alpha unbranched aldehydes are converted to alpha alkylacrolein and the 2-methylalkanals are recovered in a high purity.

25 Claims, No Drawings

PROCESS FOR THE SEPARATION OF 2-METHYLALKANALS FROM ISOMERS THEREOF

PRIOR APPLICATION

This application is a continuation of U.S. patent application Ser. No. 325,660 filed Mar. 20, 1989, now abandoned.

The present invention is directed to a process for the separation of 2-methylalkanals from their isomers. It is particularly directed to those mixtures which result from the hydroformylation of mixtures of isomeric olefins.

BACKGROUND OF THE INVENTION 2-methylalkanals are useful as intermediates for various commercial processes; e.g. they may be oxidized to the corresponding carboxylic acids which, in turn, are used as reactants in the manufacture of perfumes. The compounds obtained by the method of the present invention are also useful for the production of pharmaceuticals and plant protection agents.

The principal process for the production of aldehydes having more than two carbon atoms is the well known hydroformylation reaction. This comprises the addition of carbon monoxide and hydrogen to olefins in the presence of metal carbonyl compounds as catalysts. Thus far, only cobalt and rhodium have been found suitable for this purpose.

This reaction generally produces a mixture of isomeric aldehydes. In particular, n-aldehydes and their isomers, as well as α-methylaldehydes are formed from olefins having unsaturation on their terminal carbon atoms. In actuality, the only way to avoid the formation of mixtures is to use symmetrical or sterically inhibited olefins as starting materials.

The ratio of n-compounds to corresponding iso-compounds in the formylation reaction product varies within wide ranges. This is determined by the particular catalysts and the reaction conditions used.

A further complicating factor resides in the source of the olefinic starting materials. They normally come from the processing of crude oil and frequently contain mixtures of olefins, rather than individual compounds in a pure or nearly pure state; such mixtures usually contain olefins having the same number of carbon atoms, but with different structures.

For example, when mixtures of 2-methylbutene-1 and 2-methylbutene-2 are hydroformylated, the resultant products include 2,3-dimethylbutanal, 3-methylpentanal and 4-methylpentanal. Correspondingly, mixtures of 3-methylpentene-2 and 2-ethylbutene-1 will yield 2,3-dimethylpentanal, 3-ethylpentanal, and 4-methylhexanal.

Heretofore, the aldehyde mixtures referred to were separated by fractional distillation. However, this presents a problem because most of these aldehydes are extremely sensitive to oxidation. They tend to condense to form higher molecular weight secondary products and to decompose thermally.

Therefore, it is necessary to observe a number of precautions in carrying out these distillations. As would be expected, the sensitive aldehydes are distilled at as low a temperature as possible and only after complete removal of the catalysts. Variations of the process use azeotropic and extractive distillation methods in order to avoid the unwanted decomposition and/or condensation.

The separation is made more difficult by the fact that the hydroformylation reaction results in aldehydes having the same number of carbon atoms and, therefore, they possess boiling points which differ only slightly. To successfully separate these compounds by distillation, it is necessary to use columns having extremely high selectivity and to use very high reflux ratios. Such requirements are not compatible with cost-effective separation and there is often a substantial reduction in yield due to the fact that, in spite of all the precautions, higher boiling compounds are formed from the n-aldehydes which are of low thermal stability.

THE PRIOR ART

The need for the particular aldehydes in question, coupled with the difficulties set forth herein, has engendered substantial efforts to develop processes which permit the separation of such mixtures simply and effectively. For example, DE 28 33 538 C2 describes the separation of α-methylalkanals having straight-chain alkyl groups with 7 to 12 carbon atoms from straight-chain compounds with the same number of carbon atoms which are unsubstituted in the alpha position. This is carried out by thermal treatment in a distillation column. The branched aldehydes distill off, while the straight-chain aldehydes are converted into substantially non-volatile compounds and remain in the residue. As far as it goes, this process works, but it will be apparent that the straight-chain aldehydes are substantially discarded. Therefore, it is of value *only* when the straight-chain aldehydes are of little or no value.

DE 24 59 152 C2 teaches the recovery of pure n-aldehydes from isomeric mixtures by treatment with alkali metal hydrogen sulfite. The sulfite is added in stoichiometric or sub-stoichiometric amounts and causes the n-aldehydes to precipitate as the corresponding hydrogen sulfite addition compounds. The precipitate is separated, washed, and then split in the usual manner. While this process is taught as being suitable for separation of mixtures resulting from the hydroformylation process, it is quite expensive due to the substantial amounts of chemicals used. Therefore, it is commercially useful only for the recovery of n-aldehydes which are of great value.

A similar process is described in DE 960 187 C1. Here, mixtures of isomeric aldehydes are separated by the use of hydrogen sulfite compounds. Thus, the mixture is first treated with an aqueous solution of neutral sulfite and an approximately equivalent amount of a weakly acid compound. The resultant mixture of hydrogen sulfite compounds is then subjected to gradual heating so that the temperature thereof increases slowly. The aldehydes are released in succession in accordance with their increasing boiling points. Each is withdrawn and the residue, after cooling, is reused for the preparation of hydrogen sulfite compounds.

However, this process can be used only for the separation of low molecular weight aldehydes which are sufficiently volatile to distill off at very low temperatures. The high aldehydes decompose substantially at their boiling points and, therefore, cannot be separated in this manner.

A still further process for the separation of n-aldehydes is set forth in DE 22 18 305. The mixtures are treated with non-oxidizing strong mineral acids. This converts the straight-chain aldehydes into 1,3,5-trioxanes which are separated by fractional crystallization. Thereafter, the separated trioxanes are depolymerized in distillation equipment with the addition of small amounts of phosphorous (V) oxide.

This process relies on different crystallizability and solubility of the trimeric n-alkanals and iso-alkanals. However, if both the n-alkanals and the iso-alkanals are crystalline, this process is inoperable, hence, severely limiting its applicability and usefulness.

BRIEF DESCRIPTION OF THE PRESENT INVENTION

As can be seen from the foregoing, it is desirable to develop a process whereby 2-methylalkanals can be separated from mixtures of isomeric aldehydes. Typically, such mixtures result from the hydroformylation of isomeric olefins.

The solution to this problem is the process of the present invention which comprises distilling the isomeric aldehyde mixture in the presence of formaldehyde and an aldolization catalyst.

It is well recognized that aldehydes having a methylene group alpha to the carbonyl can be reacted with formaldehyde to form the 2-methylene aldehydes. The reaction normally takes place under pressure and—depending on the selected temperature—with residence periods which range from a few seconds to hours.

Aldehydes which are monosubstituted or unbranched at the alpha position are highly reactive. Therefore, it is surprising that the present invention is able to separate the α-unbranched aldehydes from the corresponding α-monobranched aldehydes by a selective reaction.

DETAILED DESCRIPTION OF THE PRESENT INVENTION

The present process is directed to the recovery of 2-methylalkanals from mixtures of their isomeric aldehydes. The process is especially useful as applied to mixtures resulting from the hydroformylation of olefin isomers. Herein, the terms olefin isomers and isomeric olefins are intended to indicate compounds which differ from each other in the arrangement of the atoms or the position of the double bond in the molecule.

Typically, olefin isomers, from which the isomeric aldehydes to which the present invention is directed are derived, are products of the dehydration of 2-methylbutanol or 2-ethylbutanol. The aldehyde mixtures resulting from the foregoing olefins have approximately the following composition.

| components | wt. % |
|---|---|
| 2-methylbutene-1/2-methylbutene-2 mixtures | |
| 3-methylbutene-1 | 0.5–4% |
| pentenes | 0.5–5% |
| 2-methylbutene-1 | 50–85% |
| 2-methylbutene-2 | 15–30% |
| others | 0.5–5% |
| 3-methyl-2-pentene/2-ethylbutene-1 mixtures | |
| C4–C5 olefins | 0.5–2% |
| hexenes | 0.5–4% |
| 2-ethylbutene-1 | 5–10% |
| trans-3-methyl-2-pentene | 20–40% |
| cis-3-methyl-2-pentene | 40–60% |

The foregoing is exemplary only and it is understood that other olefin mixtures can also be hydroformylated and used for recovery of 2-methylalkanals in accordance with the present process.

The process of hydroformylating olefins is well recognized in the art. Numerous variations are used and the reaction can be carried out in the presence of cobalt or rhodium catalysts. A comprehensive description of this reaction can be found, for example, in New Sythesis with Carbon Monoxide, Edited by J. Falbe, Springer Verlag 1980.

Typically, the olefin mixtures are hydroformylated with rhodium as a catalyst at 90° to 140° C. and 20 to 30 MPa. When this is carried out, the resultant aldehyde mixtures have approximately the following composition, after separation of the catalyst by flash distillation on a thin-layer evaporator.

| aldehyde mixture on the basis of 2-methylbutene-1/2-methylbutene-2 | |
|---|---|
| 2,3-dimethylbutanal | 55–80% |
| 3-methylpentanal | 10–30% |
| 4-methylpentanal | 3–12% |
| others | 1–4% |
| aldehyde mixture on the basis of 3-methyl-2-pentene/2-ethylbutene-1 | |
| 2,3-dimethylpentanal | 55–90% |
| 3-ethylpentanal | 5–15% |
| 4-methylhexanal | 5–15% |
| others | 0.5–2% |

To carry out the distillation reaction of the present invention, it has been found advantageous to use 1 to 2 moles of formaldehyde per mole of α-unbranched aldehyde; 1.1 to 1.4 moles per mole of unbranched aldehyde is more desirable. It is useful to add the formaldehyde in the form of a solution. An aqueous solution is most preferred, but alcohol and other solvents may also be used. Polymerized formaldehyde (e.g. paraformaldehyde) is also suitable. Normally, all of the formaldehyde is added to the reaction mixture at the beginning of the reaction. It is also possible, on the other hand, to add it portionwise in stages.

As aldolization catalysts, amines are used. Secondary amines are preferable, especially those of the formula $$R^1NH-R^2$$

wherein $R^1$ and $R^2$ are individually alkyl groups having 1 to 12 carbon atoms. Preferably, the alkyl groups have 3 to 5 carbon atoms and, most preferably, di-n-butylamine is recommended.

It has been found advantageous to carry out the reaction in the presence of additives which are monocarboxylic acids or polycarboxylic acids. The former should have 1 to 10 carbon atoms and the latter 2 to 10 carbon atoms. Monocarboxylic acids having 3 to 5 carbon atoms are more preferred and n-butyric acid is most desirable. The di- and polycarboxylic acids may be aromatic, araliphatic and, most preferably, aliphatic. It has been found that acetic acid, propionic acid, n-butyric acid, iso-butyric acid, oxalic acid, succinic acid, and tartaric acid are suitable.

As to concentration, 0.025 to 0.3 moles of amine per mole of α-unbranched aldehyde operates well. Preferably, the amine should be present in an amount of 0.1 to 0.2 moles per mole of α-unbranched aldehyde. As to the carboxylic acids, 0.05 to 0.5 equivalents per mole of α-unbranched aldehydes works quite well. It has been found that 0.15 to 0.3 equivalents per mole of α-unbranched aldehyde is more desirable.

When the formaldehyde reacts with the α-unbranched aldehydes, α-methylol aldehydes are formed. However, these compounds are generally unstable and decompose to form the corresponding α-methylene aldehydes (α-alkyl acroleins) and water is split out during the course of this reaction. There are very substantial differences in boiling points between the α-methylene aldehydes and the α-methyl aldehydes which contain one carbon atom less; therefore, distillation separation of the aldehydes is relatively simple and easy.

It is a feature of the present invention that the aldehyde mixture is reacted with formaldehyde during distillation. Because of the ease of distillation, no particular special apparatus is required. The invention has been practiced with columns packed with glass rings or metal heliocoils; the number of theoretical plates is advantageously 9 to 72 and preferably 24 to 36. As will be apparent to the person of ordinary skill, the reflux ratio depends upon the type of column used. In a packed column having 24 theoretical plates, the reflux ratio has been set at 5 parts reflux to 1 part withdrawn overhead. The temperature of the bottoms also depends upon the column, but these matters are well recognized by persons of ordinary skill in the art.

By following the present process, 2-methylalkanals can be obtained in a purity in excess of 97%. In fact, the only contaminants are minor amounts of α-unbranched aldehydes and some inert materials. The latter do not interfere with the further processing of the 2-methylalkanals to, for example, acids, amines, alcohols, diols, etc. Moreover, they are easy to remove from further derivatives of the aldehyde.

The following examples are intended to illustrate the invention, but do not limit it.

EXAMPLE 1

Preparation of 2,3-dimethylbutanal

When 2-methyl-1-butene is hydroformylated and the aldehyde mixture subsequently worked up by distillation, a main fraction of the following composition is obtained:
first runnings: 1.01 wt. %
2,3-dimethylbutanal: 69.57 wt. %
3-methylpentanal: 21.13 wt. %
4-methylpentanal: 7.46 wt. %
final runnings: 0.83 wt. %

2000 g of this aldehyde mixture (5.71 moles of alpha-unbranched aldehydes) are mixed with 812.9 g of formalin (29.5 wt. % of formaldehyde, corresponding to 7.99 moles), 110.5 g of di-n-butylamine (0.86 moles) and 150.9 g of n-butyric acid (1.71 moles) and subjected to fractional distillation at 0.1 MPa with agitation. The packed column used has 24 theoretical plates. The reflux ratio is set at 5 parts of reflux per part of withdrawn overhead product. The following table contains the head and bottom temperatures of each fraction, as well as the weights of the organic and aqueous phases.

| fraction | max. temp. of the top product (°C.) | max. temp. of the bottom product (°C.) | weighed organic phase (g) | weighed aqueous phase (g) |
| --- | --- | --- | --- | --- |
| 1 | 85 | 90 | 84.1 | 24.7 |
| 2 | 87 | 96 | 1144.2 | 346.2 |
| 3 | 90 | 98 | 156.2 | 59.7 |
| 4 | 92 | 144 | 235.8 | 106.5 |
| 5 | 104 | 220 | 326.7 | 220.4 |
| residue | | | 369.8 | |

According to the gas chromatographic analyses the organic phases have the following composition:

| | Composition of the organic phase (GC analysis) (%) | | | | |
| --- | --- | --- | --- | --- | --- |
| | 1st fraction | 2nd fraction | 3rd fraction | 4th fraction | 5th fraction |
| first runnings | 11.65 | 0.85 | 0.86 | 5.38 | 4.43 |
| 2,3-dimethylbutanal | 79.22 | 97.14 | 49.50 | 27.25 | 6.51 |
| 3-methylpentanal | 0.09 | 0.01 | 0.02 | 0.08 | 0.10 |
| 4-methylpentanal | 7.04 | 1.24 | 0.01 | 0.01 | — |
| alpha-alkylacroleins | 0.03 | 0.46 | 45.83 | 64.22 | 52.76 |
| final runnings | 1.97 | 0.50 | 3.78 | 3.06 | 36.20 |

Thus 79.9% of the 2,3-dimethylbutanal used is recovered in the organic phase of the 2nd fraction in more or less isomer-free form.

EXAMPLE 2

Preparation of 2,3-dimethylpentanal

When 3-methyl-2-pentene is hydroformylated and the aldehyde mixture subsequently worked up by distillation, a main fraction of the following composition is obtained:
first runnings: 0.52 wt. %
2,3-dimethylpentanal: 77.61 wt. %
3-ethylpentanal: 10.89 wt. %
4-methylhexanal: 10.72 wt. %
final runnings: 0.26 wt. %

2000 g of this aldehyde mixture (3.78 moles of alpha-unbranched aldehydes) are mixed with 538.2 g of formalin (29.5 wt. % of formaldehyde, corresponding to 5.29 moles), 73.1 g of di-n-butylamine (0.57 moles) and 99.9 g of n-butyric acid (1.13 moles) and subjected to fractional distillation at 0.1 MPa with stirring. The packing column used has 24 theoretical plates and the reflux ratio is set at 5 parts of reflux per part of withdrawn top product. The following table contains the head and bottom temperatures of each fraction as well as the weighed amounts of organic and aqueous phase.

| fraction | max. temp. of the top product (°C.) | max. temp. of the bottom product (°C.) | weighed organic phase (g) | weighed aqueous phase (g) |
| --- | --- | --- | --- | --- |
| 1 | 140 | 180 | 1421.5 | 495.1 |
| 2 | 147 | 193 | 104.1 | — |
| 3 | 148 | 208 | 95.9 | — |
| 4 | 152 | 240 | 172.2 | — |
| residue | | | 422.4 | |

According to the gas chromatographic analyses the organic phases have the following composition:

| | Composition of the organic phase (GC analysis) (%) | | | |
|---|---|---|---|---|
| | 1st fraction | 2nd fraction | 3rd fraction | 4th fraction |
| first runnings | 1.71 | 1.61 | 1.33 | 2.16 |
| 2,3-dimethylpentanal | 97.68 | 76.71 | 13.14 | 4.62 |
| 3-ethylpentanal | 0.01 | 0.11 | 0.15 | 0.11 |
| 4-methylhexanal | 0.03 | 0.19 | 0.78 | 1.60 |
| alpha-alkylacroleins | 0.08 | 17.48 | 77.84 | 81.04 |
| final runnings | 0.49 | 3.90 | 6.76 | 10.47 |

Thus 89.5% of the 2,3-dimethylpentanal used is recovered in the organic phase of the 1st fraction in more or less isomer-free form.

What we claim is:

1. A process for the separation of 2-methylalkanals from a mixture thereof with at least one alpha unbranched aldehyde isomer thereof comprising distillation of said mixture in the presence of formaldehyde and aldolization catalyst wherein said formaldehyde reacts with said mixture during distillation and wherein a selective aldolization reaction is effected in which the alpha unbranched aldehydes are converted to alpha alkyl acrolein and the 2-methylalkanals are separated therefrom and recovered in excess of 97% purity.

2. The process of claim 1 wherein said formaldehyde is present in an amount of 1 to 2 moles per mole of aldehyde unbranched in the alpha position.

3. The process of claim 2 wherein said amount is 1.1 to 1.4 moles of formaldehyde per mole of said aldehyde.

4. The process of claim 1 wherein said formaldehyde is polymerized.

5. The process of claim 1 wherein said formaldehyde is in solution.

6. The process of claim 5 wherein said formaldehyde is in water solution.

7. The process of claim 5 wherein said formaldehyde is in alcohol solution.

8. The process of claim 1 wherein said formaldehyde is added to said mixture at the beginning of said distillation.

9. The process of claim 1 wherein said formaldehyde is added to said mixture in stages.

10. The process of claim 1 wherein said catalyst is an amine.

11. The process of claim 10 wherein said amine is a secondary amine.

12. The process of claim 11 wherein said secondary amine is of the formula $$R^1-NH-R^2$$

wherein $R^1$ and $R^2$ are individually alkyl groups having 1 to 12 carbon atoms.

13. The process of claim 12 wherein said alkyl groups have 3 to 5 carbon atoms.

14. The process of claim 13 wherein said catalyst is di-n-butyl amine.

15. The process of claim 10 wherein said amine is present in an amount of 0.025 to 0.3 moles per mole of alpha unbranched aldehyde.

16. The process of claim 15 wherein said amount is 0.1 to 0.2 moles per mole of alpha unbranched aldehydes.

17. The process of claim 1 wherein there is futher present an additive selected from the class consisting of monocarboxylic acids having one to ten carbon atoms, polycarboxylic acids having two to ten carbon atoms, and mixtures thereof.

18. The process of claim 17 wherein said monocarboxylic acid has 3 to 5 carbon atoms.

19. The process of claim 17 wherein said additive is selected from the class consisting of aromatic acids, araliphatic acids, aliphatic acids, and mixtures thereof.

20. The process of claim 19 wherein said additive is an aliphatic acid.

21. The process of claim 20 wherein said acid is n-butyric acid.

22. The process of claim 17 wherein said additive is selected from the class consisting of acetic, propionic, n-butyric, i-butyric, oxalic, succinic, and tartaric acids.

23. The process of claim 17 wherein said additive is present in an amount of 0.05 to 0.5 equivalents per mole of alpha unbranched aldehyde.

24. The process of claim 1 wherein said distillation is carried out in a distillation column having 9 to 72 theoretical plates.

25. The process of claim 24 wherein said column has 24 to 36 theoretical plates.

* * * * *